United States Patent [19]

Lucchesi

[11] 4,048,335

[45] Sept. 13, 1977

[54] METHOD OF INHIBITING MYOCARDIAL ISCHEMIA IN MAMMALS USING QUATERNARY SALTS

[75] Inventor: Benedict R. Lucchesi, Ann Arbor, Mich.

[73] Assignee: The Regents of the University of Michigan, Ann Arbor, Mich.

[21] Appl. No.: 715,961

[22] Filed: Aug. 19, 1976

Related U.S. Application Data

[60] Division of Ser. No. 480,114, June 17, 1974, Pat. No. 4,001,327, which is a continuation-in-part of Ser. No. 269,128, July 5, 1972, Pat. No. 3,840,666.

[51] Int. Cl.$^2$ .................. A61K 31/14; A61K 31/685
[52] U.S. Cl. ..................................... 424/329; 424/199
[58] Field of Search ............................. 424/329, 199; 260/567.6 M

[56] References Cited

U.S. PATENT DOCUMENTS 3,452,102  6/1969  Lednicer ...................... 260/567.6 M
3,658,815  4/1972  Fouche ......................... 260/567.6 M Primary Examiner—Albert T. Meyers
Assistant Examiner—Daren M. Stephens
Attorney, Agent, or Firm—John J. McDonnell

[57] ABSTRACT

1-(N-isopropyl-N,N-dimethylamino)-3-(1-naphthoxy)-propan-2-ol quaternary salts are useful cardiovascular agents as evidenced by their potent and long-acting anti-arrhythmic, anti-fibrillatory and myocardial ischemia-inhibitory activity. They, furthermore, lack the undesirable side-effects, e.g. β-adrenergic receptor blocking and local anesthetic activity, characteristic of related prior art compounds.

4 Claims, No Drawings

METHOD OF INHIBITING MYOCARDIAL ISCHEMIA IN MAMMALS USING QUATERNARY SALTS

This application is a division of application Ser. No. 480,114, filed June 17, 1974, now U.S. Pat. No. 4,001,327; and which is a continuation-in-part of applicaton Ser. No. 269,128 filed July 5, 1972, now U.S. Pat. No. 3,840,666.

The present invention is concerned with novel chemical compounds of the following formula

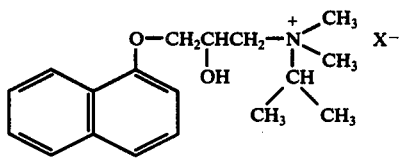

wherein X⁻ is the anion of a pharmaceutically acceptable non-toxic acid and also with novel methods for their utilization as cardiovascular agents.

Anions of suitable pharmaceutically acceptable non-toxic acids are typified by the halides, e.g. chloride, bromide, iodide, fluoride, the ortho-, meta- and pyro-phosphates, the sulfate and the alkylsulfates such as methylsulfate and ethylsulfate.

Particulary preferred anions for the purposes of this invention are the iodide and the chloride.

The compounds of the present invention are conveniently manufactured by a variety of methods. For example, a tertiary amine of the following structural formula

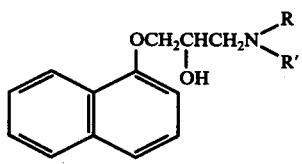

wherein R and R' can be methyl radicals or R can be a methyl radical and R' an isopropyl radical are contacted with the appropriate alkyl halide, alkyl sulfate or alkyl phosphate. As a specific example of this process, 1-(N-isopropyl-N-methylamino)-3-(1-naphthoxy)propan-2-ol is contacted with methyl iodide in acetone, to afford 1-(N-isopropyl-N-methylamino)-3-(1-naphthoxy)propan-2-ol methiodide. On the other hand, 1-(N,N-dimethylamino)-3-(1-naphthoxy)propan-2-ol may be treated with isopropyl iodide to afford the identical product.

An alternate method for the manufacture of the instant compounds involves reaction of a secondary amine of the following structural formula

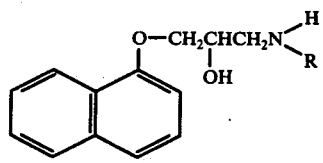

wherein R is a methyl or isopropyl radical with the appropriate alkyl halide, alkyl sulfate or alkyl phosphate. Typically, 1-(N-isopropylamino)-3-(1-naphthoxy)propan-2-ol is contacted with two molecular equivalents of methyl chloride to yield 1-(N-isopropyl-N-methylamino)-3-(1-naphthoxy)propan-2-ol methochloride.

The compounds of the present invention are useful in consequence of their potent and long-acting cardiovascular activity. Thus, they possess, for example, anti-arrhythmic, anti-fibrillatory and myocardial ischemia-inhibitory properties. Myocardial ischemia occurs in conditons such as angina pectoris and myocardial infarction. These agents, furthermore, possess the advantages over prior art compounds of lacking undesirable side-effects such as β-adrenergic receptor blocking and local anesthetic activity.

These unexpected and surprising advantages are illustrated by the β-adrenergic receptor blocking activity of 1-(N-isopropylamino)-3-(1-naphthoxy)propan-2-ol described by Lucchesi et al., *Canadian Journal of Physiol. Pharmacology*, 44, 543 (1966) and Lucchesi et al., *N.Y. Acad. of Sci.*, 139, 940 (1967) and the local anesthetic activity of 1-(N,N-diethylamino)-3-(1-naphthoxy)propan-2-ol methiodide, described by Lucchesi et al., *J. Pharm. and Exper. Therap.*, 162, 49 (1968).

Preferred compounds of the present invention are the quaternary methiodide and methochloride salts of 1-(N-isopropyl-N-methylamino)-3-(1-naphthoxy)propan-2-ol. The methochloride quaternary salt is especially advantageous in consequence of its lack of undesirable side-effects characteristic of related compositions. Thus, it does not suffer from the disadvantage of inducing iodism, i.e. chronic iodide poisoning, which can occur as a result of the administration of iodides.

The cardiovascular properties of the instant compounds are evidenced by their activity in the following assays:

For determination of anti-arrhythmic properties, the following assays are used.

ACETYLSTROPHANTHIDIN-INDUCED ARRHYTHMIAS IN THE RABBIT ISOLATED HEART

The rabbit isolated heart is perfused according to the Langendorff method. Male rabbits, 1.8 to 2.2 kg., are killed by cervical dislocation and their hearts are removed quickly. The perfusion solution is of the following composition, expressed as millimoles per liter: NaCl, 171.1; KCl, 2.8; $CaCl_2 . 2H_2O$, 2.0; $MgCl_2 . 6H_2O$, 2.1; dextrose, 10.0; and THAM buffer, 4.1. The final solution is adjusted to a pH of 7.4 by the addition of 1 N HCl. The heart is enclosed in a double-walled glass chamber; the heart and perfusion medium are maintained at a temperature of 30° C. The perfusion solution is recycled and oxygenated by passing 100% oxygen into the reservoir containing the perfusion solution. Electrocardiographic recordings are made on a polygraph. The method has been described previously in greater detail by Lucchesi and Hardman, *J. Pharmacol Exp. Therap.*, 132, 372 (1961).

OUABIN-INDUCED ARRHTHMIAS IN THE ANESTHETIZED DOG

Male mongrel dogs, 8.3 to 12.9 kg. in weight, are anesthetized with a mixture of allobarbitol (60 mg./kg.) urethane (240 mg/kg.) and monethylurea (240 mg./kg.). (Dial-Urethane Solution, Ciba). Blood pressures are measured from the femoral artery with a pressure transducer. All drugs are administered into the cannulated left external jugular vein. The right vagus is sectioned and its distal end is stimulated with 1.0 msec. square-wave stimuli at a frequency of 40 cps at 6.0 to 8.0 V.

Ventricular tachycardia is induced by the administration of ouabain, 40 mg./kg. i.v., followed in 30 min. by 20 mg./kg. and every 15 min. thereafter by an additional 10 mg./kg. until ventricular tachycardia develops (Lucchesi and Hardman, 1961).

The criteria used to determine antiarrhythmic activity are (1) reversion to normal sinus rhythm for a period of not less than 30 min.; and (2) the failure of right vagal stimulation to expose automatic ectopic ventricular activity during the period of vagal-induced sino-artrial nodal arrest.

Lead II electrocardiograms are monitored continuously on an oscilloscope and all recordings are made on a polygraph.

VENTRICULAR ARRHYTHMIAS AFTER CORONARY ARTERY LIGATION a. One-step Ligation

Dogs are anesthetized with pentobarbital sodium, 30 mg./kg. i.v. The heart is exposed through the 5th left intercostal space. A suture is passed under the left anterior descending coronary artery, near its origin. The free-ends of the suture are passed through a short section of polyethylene tubing. The artery can then be occluded by pressing the tubing onto the vessel, while at the same time pulling up on the free ends of the suture. The occlusion can be terminated by releasing the suture and pulling the tubing away from the vessel. In these experiments, acute occlusion of the anterior descending coronary artery is maintained for a period of 10 min., and if the animal survives, the occlusion is released.

Three different experiments are used on dogs studied in this fashion. In the first set of experiments, the animals are divided into control and test groups. The test group receives test compound prior to the occlusions. One to three 10 min. occlusions (with a 10 min. interval between occlusions) are performed depending on when and if ventricular fibrillation develops. The control group receives a comparable volume of 0.9% sodium chloride solution, and occlusions are performed in the same manner as in the test group. A similar study, using this technique has been described previously by Lown and Wolf, Circulation, 44, 130 (1971).

In the second set of experiments, the test compound is administered at a constant infusion rate of 2.5 mg./min. When a total dose of 5 mg/kg. is attained, the left coronary artery is occluded, while still maintaining drug infusion at the constant rate. The occlusion is released after 10 minutes, and drug infusion is discontinued when the animal demonstrates normal sinus rhythm, usually 2 to 3 minutes after resumption of blood flow. After a stabilization period of 2 hours, a volume of 0.9% saline, equivalent to that of drug previously received, is administered at a constant rate, i.v. The anterior descending artery is occluded again for 10 minutes, and then released. If fibrillation ensues, it is converted electrically to a normal rhythm. Finally, 30 minutes after initiation of normal sinus rhythm, the test compound is administered again as previously described, and the anterior descending artery is occluded for 10 minutes and released. The control group of this series is treated indentically, with saline being infused at all times in place of drug.

The third set of experiments deals with the anti-fibrillatory effects of test compound after release of a 20 minute occlusion of the anterior descending coronary artery. Animals are prepared and drug is infused as previously outlined. This group of animals is compared to a control group, which receives a saline infusion in place of test compound.

Finally, both 10 and 20 minute occlusions are done in the presence of propanolol, which is administered at an infusion rate and dose identical to that of test compound.

In all experiments, each dog is respired with room air by means of a respirator. Femoral arterial pressure is measured with a pressure transducer. All drugs are administered via the left external jugular vein. Lead II EKG and all other recordings are made on a polygraph.

b. Two-step Ligation

Dogs are anesthetized with pentobarbital sodium, 30 mg./kg. i.v. A cuffed endotracheal tube is inserted and the animals are ventilated artificially with room air by a respirator. The heart is exposed by entering the chest through a left thoracotomy incision in the fourth interspace. A 2 cm. incision is made in the pericardium to expose the anterior descending coronary artery and a two-stage ligation is performed according to the method described by Harris, Circulation, 1, 1318 (1950). The animals are studied 48 hours post-infarction, in the unanesthetized state, while supported in a sling and maintained in a quiet environment, during the phase of spontaneous ventricular arrhythmias.

All drugs are administered into the brachiocephalic vein, and the Lead II electrocardiogram is monitored on an oscilloscope and recorded on a polygraph. The electrocardiographic recordings are analyzed according to the method of Moran et al., J. Pharmacol. Exp. Therap., 136, 327 (1962), in which only beats of S-Z nodal origin are considered as normal and all other QRS complexes are classified as ectopic.

Their anti-fibrillatory properties are detected by the following assay.

Experiments are performed on mongrel dogs anesthetized with pentobarbital sodium administered intravenously at a dose of 30 mg./kg. The chest is opened by a left thoracotomy incision and the heart is suspended in a pericardial cradle. The sinus node is crushed and the heart rate kept constant by electric pacing by means of an electrode sutured to the right ventricle. Vulnerability to fibrillation is assesed in the control state and repeated 30 and 60 minutes after the intravenous administration of the test compound.

The body surface electrogram is recorded from electrodes placed on the neck and left leg. To measure vulnerability to fibrillation, stimuli are delivered through silver- silver chloride electrodes sutured to the right ventricle. The stimulator used to deliver trains of 60 Hertz, 5 milliampere stimuli of 2 millisecond duration is coupled to the pacing stimulator so that the trains of 60 Hertz stimuli have onset immediately after the QRS complex and are delivered every fourth to sixth basic driving stimulus. At least 3 trains of 60 Hertz of each duration are delivered before the duration of the train is increased. The trains are prolonged by 10 second increments until fibrillation occurs. The hearts are defibrillated with (n5 to 10 seconds with direct current electric shocks. After control fibrillation threshholds have been determined, the animals are given the test compound and threshhold determinations repeated at 30 and 60 minutes after administration. A comparable study is done in a group of control dogs which receive only 0.9% saline. Over the time course of the control experiment the threshhold to electric fibrillation does not change significantly.

The myocardial ischemia-inhibitory properties of the compounds of this invention are demonstrated by their activity when tested in the following assay procedures:

A group of 10 mongrel dogs, weighing 11-19 kg., is anesthetized by the intravenous administration of 30 mg./kg. of pentobarbital sodium and breathing maintained by means of a Harvard respirator. A thoractomy is performed through the fifth left intercostal space; the heart is suspended in a pericardial cradle; a branch of the left anterior descending coronary artery is dissected free and a suture placed under that vessel. Occlusion of that arterial branch is accomplished by passing the free ends of the suture through a short section of polyethylene tubing and pressing the tubing against the vessel while exerting traction on the free ends of the suture. Termination of the occlusion is achieved by releasing the suture and pulling the tube away from the vessel.

The degree of myocardial ischemic injury resulting from occlusion of the artery is determined by the epicardial electrocardiographic method described by Maroko et al., *Circulation,* 43, 67-82 (1971). An acrylic plaque containing six embedded silver-silver chloride electrodes is sutured to the anterior lateral surface of the left ventricle and sites within the area supplied by the coronary branch that was occluded are selected for recording. All surface collateral vessels are ligated and the unipolar electrograms from the six epicardial leads and the Lead II electrocardiogram are recorded on a Grass model 7 polygraph. The sum of the ST segment elevation in the six epicardial leads (EST) is used as the index of tissue injury.

The reproducibility of the method with respect to the magnitude of EST is determined by successive 10-minute occlusions in a group of five dogs.

In a second group of five animals, the artery is occluded for a period of 10 minutes, the EST elevation is measured; the occlusion is terminated; and, 15 minutes prior to the second occlusion, the selected dose of the test compound is administered intravenously. The compound is rated active if there is a statistically significant reduction in the EST elevation as compared to that produced during the initial 10 minute occlusion period.

When 1-(N-isopropyl-N-methylamino-3-(1-naphthoxy)propan-2-ol methochloride was tested in the latter assay, at a dose of 10 mg./kg., the control EST was reduced from $34.8 \pm 4.9$ mV to $11.3 \pm 2.1$ mV.

A group of 5 mongrel dogs is anesthetized and thoractomized by the procedure described in the preceding assay and the left anterior descending and circumflex coronary arteries are cannulated and perfused with arterial blood at a constant pressure. Coronary arterial and venous blood samples are collected and their oxygen content measured. Myocardial oxygen consumption is calculated and expressed as ml./min./100 g. of the left ventricle. The mean control oxygen consumption in these 5 animals is $11.7 \pm 1.9$.

In a second group of 5 animals, prepared as described above, the selected dose of the test compound is administered intravenously prior to perfusion. The myocardial oxygen consumption is calculated and compared with the corresponding value in the control group. A compound is rated active if it effects a statistically significant reduction in the myocardial oxygen consumption observed in the control group.

1-(N-isopropyl-N-methylamino)-3-(1-naphthoxy)propan-2-ol methochloride, administered intravenously at a dose of 10 mg./kg., effected a statistically significant ($p<0.05$) reduction in myocardial oxygen consumption to a value of $7.6 \pm 1.1$.

In a separate assay, hearts are excised from anesthetized animals and perfused via the aorta at a constant pressure with oxygenated whole blood supplied by a donor dog connected to the heart. Oxygen consumption is calculated and expressed as ml./min./100 g. of the myocardium. The donor dogs are then treated intravenously with the selected dose of the test compound and the mean oxygen consumption value again calculated. The test compound is rated active if it effects a statistically significant reduction in that value.

In the latter assay, the intravenous administration of 1-(N-isopropyl-N-methylamino)-3-(1-naphthoxy)propan-2-ol methochloride to 5 donor dogs at a dose of 10 mg./kg. resulted in a statistically significant ($p<0.01$) reduction of the mean oxygen consumption value from $3.1 \pm 0.2$ to $2.1 \pm 0.1$.

The lack of significant $\beta$-adrenergic receptor blocking and local anesthetic side-effects is determined by the following assays:

TESTS FOR BETA-ADRENERGIC RECEPTOR BLOCKADE a. Isolated Atrial Strips

Experiments are performed on atrial strips prepared from right atria removed from rabbits after cervical dislocation. The atrial strips are suspended in a 50 ml. organ bath filled wih a modified Chenoweth-Koelle solution to which ethylene diamine tetraacetic acid, 1 mg.% (disodium sald) and ascorbic acid, 2 mg.%, has been added. The solution is of the following composition, expressed as millimoles per liter: NaCl, 120.0; KCl, 5.6; $CaCl_2 . 2H_2O$, 2.2; $MgCl_2 . 6H_2O$, 2.2; dextrose, 10.0; and $NaHCO_3$, 25.0. The final solution is adjusted to a pH of 7.4 by the addition of $NaHCO_3$. The solution is bubbled with 95% $O_2$ and 5% $CO_2$ and maintained at a temperature of $36° \pm 1°$ C. One end of the atrium is fixed to a stainless steel rod; the other end is tied to a force displacement transducer with a short segment of 4-0 surgical silk. The atrial strips are allowed to beat spontaneously in the bath, and measurements of peak rate are made after each dose of isoproterenol.

The muscles are allowed to stabilize for 45 min. prior to the addition of drugs to the organ bath. Cumulative concentration-effect curves for isoproterenol are determined on control strips, on atrial strips exposed for 1 hours to test compound, $10^{-6}M$, and on atrial strips exposed for 1 hour to test compound $10^{-4}M$. Changes in rate are calculated as a percentage of maximal atrial rate. Probit analysis, as described by Goldstein, Biostatistics: *An Introductory Text,* 153-174, The MacMillan Company, New York (1964), is used to compute the effective-dose-50% ($ED_{50}$) for each concentration-effect curve, and these values in turn are used to calculate the $pA_2$ value of test compound, according to the method described by Schild, *Brit. J. Pharmacol.* 2, 189 (1957).

b. Anesthetized Dog Preparation

Dogs are anesthetized wih Dial-Urethane. The right ventricle was exposed through the 5th right intercostal space; the pericardium is opened and a strain gauge arch is sewn to the right ventricle. The muscle segment between the feet of the stain gauge arch is stretched to a length which gave a contraction of maximal amplitude.

The animals are respired with room air by means of a respirator. Femoral arterial pressure is measured with a pressure transducer. Drugs are administered into the left external jugular vein and recordings are made on a polygraph.

Changes in isometric tension to geometrically increasing doses of isoproterenol administered i.v. are determined before and after test compound. Each dog thus serves as its own control. Statistical analysis of the data are performed by the method of paired comparisons as described by Hill, *Principles of Medical Statistics*, 143-151, 172 Oxford University Press, New York (1961).

TESTS FOR INTRINSIC PROPERTIES a. Isolated Atrial Strips

Isolated right atria from 9 rabbits are used (weight 2.2-2.8 kg.). The atria are permitted to equilibrate for 30 minutes and the spontaneous atrial rate is recorded every 10 min. for the next 60 min. When the atrial rate has stabilized, the preparation is exposed to test compound in concentrations ranging from $10^{-M}$ to $10^{-3}M$ inclusive. Subsequent addition of test compound is made at 30 minute intervals. The spontaneous atrial rate is determined every 10 minutes.

b. Anesthetized Dog Preparation

Dogs, anesthetized with Dial-Urethane are used to test the effects of the drug on resting heart rate and force of contraction. The heart is exposed via a right thoracotomy and a strain gauge arch is sutured to the right ventricle. Heart rate is recorded with a tachograph. All recordings were made on a polygraph.

c. Locla Anesthetic Activity

Female frogs (*Rana pipiens*) are decapitated and the sciatic-tibialperoneal nerves (sciatic trunk) are removed bilaterally and placed in frog Ringer's solution. The Ringer's solution is of the following composition, expressed as millimoles per liter: NaCl, 111; KCl, 2.7; $CaCl_2 \cdot 2H_2O$, 1.4; and $NaHCO_3$, 2.4. The solution nad a pH of 7.4 and is maintained at a temperature of 25° C. In one series of experiments the epineurium of the nerve is removed by the method of Feng and Liu, *J. Cell. Comp. Physiol.* 34, 1 (1949).

The experimental design has been described in greater detail previously by Lucchesi and Iwami, *J. Pharmacol. Exp. Therap.*, 162, 49 (1968). Briefly, a sciatic trunk is passed through a plastic T-tube, and both are mounted on platinum electrodes in a nerve chamber with a humidified atmosphere. Ringer's solution can then be pumped at a constant rate into the vertical limb of the T-tube. The pump also serves to remove fluid from the chamber at this same rate.

Monophasic spikes are recorded by crushing that part of the nerve in contact with the distal recording electrode. The nerves are stimulated at their peripheral ends so as to produce a maximal spike potential for the A $\alpha$ group of fibers: Since the height of the spike is an index of the number of fibers conducting impulses, and since the response is maximal, any reduction in spike height can be attributed to a block of some fibers in the treated segment. The action potential is amplified through a preamplifier, displayed on a oscilloscope and photographed. Spike potentials are photographed every 15 min. for 1 hour, starting with the time drugs are applied to the nerve trunks. The percent change from control spike amplitude is calculated from the photographed tracings.

The compound solutions employed in the above assays are prepared in the following manner:

Crystalline acetylstrophanthidin is dissolved in the perfusion medium used in the Langendorff preparation; the final concentration of the stock solution is 80 $\mu g./ml.$ Solutions of ouabain are prepared by dissolving the crystalline material in 0.9% sodium chloride solution to give a final concentration of 80 $\mu g./ml.$ Solutions of isoproterenol are made daily from 1-isoproterenol bitartrate (Sigma Chemical Co., St. Louis, Mo.) dissolved in a solution of ascorbic acid, 1 mg.%. Procaine HCl is dissolved in Ringer's solution in a concentration of $10^{-3}M$. Solutions of test compound are made daily by dissolving the crystalline material in 0.9% NaCl solution to give a final concentration of 5 mg./ml. for the intact dog experiments. For the isolated tissue experiments, test compound is dissolved in the respective perfusion media appropriate for the particular experiment.

The novel compounds of this invention are preferably administered in the form of a composition consisting of the active ingredient combined with a pharmaceutically acceptable carrier. These compositions can be administered either orally or parenterally. For oral administration tablets, lozenges, capsules, dragees, pills or powders are suitable, while aqueous solutions, non-aqueous solutions or suspensions are appropriate for parenteral administration. Acceptable pharmaceutical carriers are exemplified by gelatin capsules, sugars such as lactose or sucrose, starches such as corn starch or potato starch, cellulose derivatives such as sodium carboxymethyl cellulose, ethyl cellulose, methyl cellulose or cellulose acetate phthalate, gelatin, talc, calcium phosphate such as dicalcium phosphate or tricalcium phosphate, sodium sulfate, calcium sulfate, polyvinylpyrrolidone, acacia, polyvinyl alcohol, stearic acid, alkaline earth metai stearates such as magnesium stearate, vegetable oils such as peanut oil, cottonseed oil, sesame oil, olive oil, corn oil or theobroma, water, agar, alginic acid, benzyl alcohol, isotonic saline and phosphate buffer solutions as well as other non-toxic compatible substances.

The instant method for producing the desired cardiovascular effect in mammals comprises the administration of a therapeutically effective amount of a novel compound of this invention. The term "therapeutically effective amount" is defined as that which will produce the cardiovascular effect. For a particular subject the actual amount of compound to be used will vary with the nature of the subject, the severity of the condition, the route of administration and the particular compound used. For the inhibition of myocardial ischemia, for example, a recommended dosage range for parenteral, e.g. intravenous, administration is 1-10 mg./kg., repeated as needed. For oral administration a dosage within the range of 10-1000 mg./day is preferred.

The compounds of the present invention can be used also in combination with other known pharmaceutical agents. For example, they can be used together with known anti-anginal agents such as the long-acting nitrates, in combination with known anti-arrhythmic agents such as quinidine, and in combination with known hypotensive agents.

The invention will appear more fully from the examples which follow. They are not to be construed as limiting the invention either in spirit or in scope as variations both in materials and methods will be apparent to those skilled in the art. In the following examples, temperatures are given in degrees Centigrade (° C.) and quantities of materials in parts by weight unless otherwise noted.

EXAMPLE 1

A mixture of 11 parts of 1-(N-isopropyl-N-methylamino)-3-(1-naphthoxy)propan-2-ol, 13.6 parts of methyl iodide and 176 parts of benzene is stirred at room temperature for 3 days. The benzene layer is decanted from the oil which forms and the oil is slurried in ethanol and crystallized. The crystals are recovered by filtration and recrystallized from methyl ethyl ketone, thus affording 1-(N-isopropyl-N-methylamino)-3-(1-naphthoxy)propane-2-ol methiodide. That compound melts at about 160°–161° and is represented structurally by the following formula

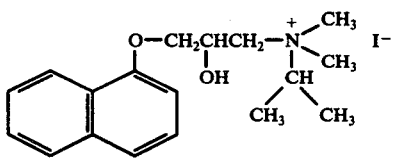

EXAMPLE 2

A mixture of 6.0 parts of 1-(N-isopropyl-N-methylamino)-3-(1-naphthoxy)propan-2-ol, 4.5 parts of methyl chloride and 40 parts of methyl ethyl ketone is allowed to stand in a steam cabinet for about 18 hours. After that time an oil forms and the mixture is cooled in an ice bath, whereupon crystallization occurs. The solid crystals are recovered by filtration and dried, then dissolved in a mixture of methanol and methyl ethyl ketone. The methanol is removed by boiling. The solution is cooled and seeded to afford pure 1-(N-isopropyl-N-methylamino)-3-(1-naphthoxy)propan-2-ol methochloride. That compound melts at about 168°–171° and is represented by the following structural formula

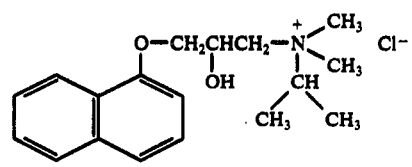

What is claimed is:

1. A method of inhibiting myocardial ischemia in mammals which comprises administering to mammals requiring inhibition of myocardial ischemia a therapeutically effective amount of a compound of the formula

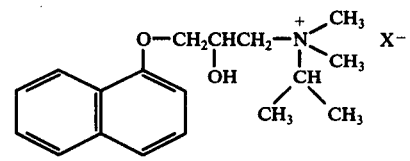

wherein X— is the anion of a pharmaceutically acceptable non-toxic acid.

2. The method of claim 1 wherein X— is a chloride, bromide, fluoride, iodide, sulfate, alkylsulfate or ortho-, meta- or pyrophosphate anion.

3. The method of claim 1 wherein the compound is 1-(N-isopropyl-N-methylamino)-3-(1-naphthoxy)propan-2-ol methiodide.

4. The method of claim 1 wherein the compound is 1-(N-isopropyl-N-methylamino)-3-(1-naphthoxy)propan-2-ol methochloride.

* * * * *